United States Patent [19]

Ikada et al.

[11] Patent Number: 5,298,243

[45] Date of Patent: Mar. 29, 1994

[54] COLONY STIMULATING FACTOR-GELATIN CONJUGATE

[75] Inventors: Yoshito Ikada; Yasuhiko Tabata, both of Uji; Hiroyasu Suzuki, Tokyo, all of Japan

[73] Assignee: Denki Kagaku Kogyo Kabushiki Kaisha, Tokyo, Japan

[21] Appl. No.: 422,701

[22] Filed: Oct. 17, 1989

[30] Foreign Application Priority Data

Oct. 20, 1988 [JP] Japan .................................. 63-262787
Jan. 24, 1989 [JP] Japan .................................... 1-13299

[51] Int. Cl.$^5$ .......................... C07K 15/00; C07K 3/02
[52] U.S. Cl. .................................... 424/85.1; 424/450; 424/492; 530/351
[58] Field of Search ................... 424/85.1, 450, 492; 530/351

[56] References Cited

U.S. PATENT DOCUMENTS 4,703,108 10/1987 Silver et al. ..................... 424/94.64

FOREIGN PATENT DOCUMENTS 230647 8/1987 European Pat. Off. ........ A61K 9/22
8809163 12/1988 European Pat. Off. ........ A61K 9/16
62-143974 6/1987 Japan ........................... C08L 101/00
62-230729 10/1987 Japan ............................ A61K 37/04

OTHER PUBLICATIONS

Derwent Pub. Ltd., London, GB: & JP-A-62 230729 (Sumitomo Pharmaceut. Co., Ltd.) Abstract.
Chemical Abstracts, vol. 103, No. 2, Jul. 1985, p. 336, col. 1, Abs. No. 11445v, Hitachi Chemical Co., Ltd. Jan. 17, 1985.
Dumont, S. et al, Eur. J. Cancer Clin. Onocol., 24, 1691 (1988).
Bartholeyns, J. et al, Anticancer Res., 8, 145 (1988).
R. Keller, Eur. J. Cancer Clin. Oncol., 25, 599 (1989).
Trinchieri et al. *Lymphokines*, vol. 14, p. 269 (1967).
Y. Tabata et al., Jpn. J. Cancer Res. (Gann), 79, 636–646, 1988.

*Primary Examiner*—Robert J. Hill, Jr.
*Assistant Examiner*—Shelly Guest Cermak
*Attorney, Agent, or Firm*—Sprung Horn Kramer & Woods

[57] ABSTRACT

Disclosed are a crosslinked gelatin microspheres containing CSF and a water soluble CSF-gelatin conjugate. Both the microspheres and the water soluble conjugate provide an improved CSF stability. They have a high potentiation on the antitumor activity of macrophages in respect of the CSF amount and the time required for macrophage activation and are effective in maintaining their activated state for a long period, compared with the native CSF. The mechanism of macrophage activation by the microspheres containing CSF is mediated via phagocytosis and different from that by native CSF, which is believed to activate macrophages via cell surface receptor. The species specificity of CSF may be abrogated when the CSF is internalized into macrophages through phagocytosis.

4 Claims, 6 Drawing Sheets

COLONY STIMULATING FACTOR-GELATIN CONJUGATE

Foreign Priority is claimed for Japanese Patent applications 63-262787 and 1-13299 filed Oct. 22, 1988 and Jan. 24, 1989, respectively.

BACKGROUND OF THE INVENTION

1. Field of the Invention

The present invention relates to colony stimulating factor (CSF)-gelatin conjugates, and processes for the production and use of the conjugates. The conjugates include cross-linked gelatin microspheres and water-soluble CSF-gelatin conjugates. Both conjugates are pharmaceutical forms useful as a tumor growth inhibitor.

2. Description of the Related Art

CSFs are substances which act on mammalian myeloid leucocyte precursor cells to promote their differentiation to granulocytes or macrophages, and which are necessary for differentiation and growth of the myeloid leucocyte precursor cells, which result in the formation of colonies comprising of neutrophil granulocytes (abbreviated as granulocyte hereinafter) or monocytes/macrophages, when the precursor cells are cultured by a two-layer agar culture method (Ichikawa, Y. et al., Proceedings of the National Academy of Science, 56, p488, 1966; Metcalf, D., Experimental Hematology 1, p185, 1972). It is known that CSFs compose of various types possessing different activities, including granulocyte-CSF (G-CSF), macrophage-CSF (M-CSF), granulocyte macrophage-CSF (GM-CSF), and multifunctional CSF (multi CSF or IL-3). Considering their functions for the differentiation and growth of leucocyte, CSFs are promising as therapeutic drugs for the treatment of leucopenia caused by the application of anticancer agents or radiation. Moreover, CSF activates mature macrophage to manifest antitumor activity (Weinberg, J.B. et al., Journal of Immunology, 121, p72, 1978; Ralph, P and Nakoing I., Cellular Immunology, 105, p270, 1978). CSFs are also promising for the treatment of cancer, and for the prophylaxis and therapy of infections caused by viruses, bacteria, and parasites because of their functions as macrophage activating factors.

However, the activity of CSFs to activate macrophages is low, and they themselves are unstable and readily degraded in vivo. Therefore, it is of prime importance to develop administration forms of CSFs aiming at an enhanced macrophage activating function and an increased stability in vivo of CSFs.

Japanese Unexamined Patent Publication (KOKAI) No. 59-46215 describes gelatin microcapsules intended for in vivo stabilization of an active component and its sustained release. However, the average diameters of microcapsules is ranging from 10 to 500 μm, and too large to be phagocytized by macrophages. Moreover, no description on microcapsules containing CSF is disclosed. Japanese Unexamined Patent Publication No. 62-230729 describes a pharmaceutical form composed of gelatin to gradually release CSF. However, since the form is produced by grinding gelatin blocks including CSF to fine powders, the resulting powders are not particles small enough to be phagocytized by macrophages. Moreover, since gelatin has not been crosslinked according to this method, and the in vitro degradation of the powders is rapid, the advantages provided by the present microspheres are not provided by the powders. Japanese Unexamined Patent Publication No. 62-143974 describes polymer microspheres containing immunopotentiators. But, the immunopotentiators used are water-soluble muramyldipeptides (MDP), their lipophilic derivatives, krestin, Nocardia rubra, interferons, lipopolysaccharides (LPS), tumor necrosis factor, pyrane copolymer, lymphokines, BCG, and the like, and do not include CSFs. In addition, the publication No. 62-143974 does not suggest a combination of the crosslinked gelatin with CSF and the combination is a new description. Y. Tabata et al., Jpn. J. Cancer Res. (Gann), 79, p636–646, 1988 describes gelatin microspheres containing interferons, but do not suggest the application of the disclosed techniques to CSF.

Generally, physiologically bioactive substances possess individual physiological activities and action mechanisms to living systems. Therefore, even if it is known that gelatin microspheres containing a physiologically bioactive substance can be phagocytized by macrophages, resulting in the appearance of its physiological action, this does not directly mean that another physiologically bioactive substance processed by the same procedure will successfully provide a similar result. Accordingly, even though it is known that gelatin microspheres containing interferon exhibit its activities through their phagocytosis by macrophages, this does not necessarily suggest that the application of the same procedure to CSF will provide the same results.

SUMMARY OF THE INVENTION

The present invention is to provide CSF-gelatin conjugates as a new pharmaceutical form aiming at an enhanced macrophage-activating activity and an improved in-vivo stability of CSFs. The CSF-gelatin conjugates include crosslinked gelatin microspheres containing CSF and water-soluble CSF-gelatin conjugates.

Further, the present invention provides a process for the production of the crosslinked CSF-containing microspheres, characterized by the steps of homogenizing an aqueous medium containing gelatin and CSF with an organic solution to form an emulsion, and subsequent crosslinking the emulsion by a crosslinking agent, and a process for the production of a water soluble CSF-gelatin conjugate, characterized by the steps of coupling CSF to gelatin in an aqueous medium with a water soluble carbodiimide to form a water-soluble conjugate.

The present invention also provides the crosslinked CSF-containing microspheres and the water soluble CSF-gelatin conjugate as a pharmaceutical preparation available for inhibiting tumor cell growth.

DESCRIPTION OF THE PREFERRED EMBODIMENTS

Crosslinked gelatin microspheres containing CSF can be prepared, for example, by the following procedure.

An aqueous solution containing gelatin and CSF is added to an organic solvent, such as toluene, chloroform, cyclohexane or a mixture thereof, containing a surfactant, followed by emulsification of the resulting mixture. The resulting emulsion is quickly poured into a precooled organic solvent containing a surfactant to form gelatin microspheres containing CSF. Subsequently, gelatin in the emulsion is crosslinked with a crosslinking agent, and the emulsion is collected by centrifugation. Sediments containing the resulting microspheres are successively washed with appropriate organic solvents and an aqueous buffer solution by centrifugation to obtain the washed crosslinked gelatin microspheres containing CSF. The CSF used in the present invention is, for example, M-CSF, GM-CSF, G-CSF or multi CSF, or a mixture thereof. Any kind of CSFs, which can be prepared by cell culturing, extraction from a biological component such as urine, ascites or the like, and by a gene recombination technique, can be employed for this procedure of the present invention. Especially, M-CSF, such as M-CSF purified from human urine as described in Japanese Unexamined Patent Application No. 61-258163 or M-CSF highly purified from a culture supernatant as described in Japanese Unexamined Patent Publication No. 1-135800, is preferably used, since they do not essentially contain impurities.

Any kind of gelatin can be used for the present invention, but it is preferable to use materials purified by hot water extraction of a crude collagen, which is prepared by an acid or alkali treatment of the bone or skin of an animal.

The mixing ratio of the gelatin and CSF is not critical, but CSF units ranging from $10^2$ to $10^9$ (n) per 1 mg gelatin is preferable. Dialdehyde compounds having excellent reactivity under room temperature such as glutalaldehyde, are preferably used, though any kind of bifunctional compounds capable of reacting with proteins can be used as crosslinking agents. The amount of glutalaldehyde used is preferably 0.01 to 2 mg, more preferably 0.05 to 1 mg per 1 mg of total proteins including CSF, gelatin, and additives.

The surfactant employed in this procedure is a noninonic surfactant such as sorbitan monooleate (Span 80), sorbitane trioleate (Span 85), or the like.

In another embodiment of the present invention, the CSF-gelatin conjugate is a water-soluble CSF-gelatin conjugate, which is prepared by linking CSF to gelatin in the presence of a condensing agent. The present water soluble CSF-gelatin conjugate is prepared, for example, by the following procedure. Gelatin is dissolved in an aqueous buffer solution, and then to the gelatin solution, CSF and subsequently a condensing agent, such as a water soluble carbodiimide, are added. The coupling reaction is carried out at a low temperature, for example, 4° C., for 5 to 30 hours. After the reaction, the reaction mixture is dialyzed or gel-filtrated to eliminate unreacted CSF and gelatin, and the resulting CSF-gelatin conjugate is then sterilized by milipose filtration.

The condensing agent used is, water-soluble carbodiimide, such as 1-ethyl-3-(3-dimethylaminopropyl) carbodiimide hydrochloride, 1-cyclohexyl-3-(2-morpholinoethyl)carbodiimide metho-p-toluenesulfphonate, and 1-benzyl-3-(3-dimethylaminopropyl)carbodiimide. Among them, the agent used most preferably is 1-ethyl-3-(3-dimethylaminopropyl)carbodiimide hydrochloride. The preferable reaction is carried out at a pH of 7 or lower than 7.

It is thought that the mechanism of the activation of macrophages by a macrophage activating agent results from an interaction between the macrophage activating agent and its specific receptor present on the macrophage surface. The mechanism of macrophase activation by the present gelatin microspheres containing CSF are different from that by the native CSF, and the macrophage activation by the CSF-contained microspheres can be concluded to be caused by the CSF gradually released from the microspheres phagocyaized in the macrophage cell. In this connection, it is preferable that the present CSF-contained microspheres have a size susceptible to the phagocytosis of the microspheres by macrophages, that is, less than 5 μm in a diameter. The size of microspheres can be controlled by changing conditions in homogenization. The homogenization methods include sonication and high pressure homogenization or the like.

The present CSF-gelatin conjugates crosslinked CSF-containing microspheres and water-soluble CSF-gelatin conjugate can be simply used for assays and therapies by dispersion or resolution in a buffer solution, physiological saline, injective medium, and the like. In addition, the conjugates can be dried for storage, prior to use.

The CSF-gelatin conjugates of the present invention have the following properties superior to those of native CSF:

(1) They potentiate the antitumor activity of macrophages much more efficient than the corresponding native CSF in respect of the CSF amount and the time required for macrophage activation; and (2) Their stability for storage is high and macrophages activated by the present CSF-gelatin conjugates maintain their activated state for a much longer than those activated by the corresponding native CSF.

In conclusion, the present CSF-gelatin conjugates can be used as an antitumor drug because of its ability to effectively activate macrophages to acquire the antitumor function. In addition, the conjugates may be expected to use as prophylactic and therapeutic drugs for infectious diseases.

EXAMPLES

The present invention will now be further illustrated by, but is by no means limited to, the following examples.

EXAMPLE 1

First, 0.25 g of sorbitan monooleate (Span 80) was dissolved in a mixture of 2.5 ml of toluene and 2.5 ml of chloroform, and to this organic solution, 0.2 ml of an aqueous solution containing 20 mg of gelatin (alkaline type, pI 4.9, Nitta Gelatine, Japan) and $1.38 \times 10^5$ units of M-CSF (abbreviated as HK-CSF) derived from mouse HK cells in Reference Example 1, was added and the mixture was homogenized by sonication (10 W, 10 seconds). The resulting emulsion was poured rapidly to 40 ml of precooled chloroform/toluene (25% : 75%) containing 2 g of Span 80. Next, a 5 ml aliquot of toluene saturated with glutaraldehyde was added to the gelatin emulsion prepared as above, and the mixture was continuously stirred at 0° C. for 6 hours. Note, the glutaraldehyde-saturated toluene was prepared by a vigorous mixing of 10 ml of 25% aqueous glutaraldehyde solution with 10 ml of toluene. The concentration of glutaraldehyde in toluene was determined to be 1.12 mg/ml, by a method of Sawicki, E., Analytical Chemistry, 33, 93–96, 1961 using 3-methyl-2-benzothiazolinone hydrazone. The above-mentioned emulsion was centrifuged at 4000 rpm for 5 minutes to collect the resulting crosslinked gelatin microspheres containing CSF. The microspheres were successively washed with 25% chloroform in toluene, isopropanol, and phosphate-buffered saline solution (PBS), by centrifugation and this was repeated four times. Finally the washed CSF-contained gelatin microspheres were suspended in PBS. The amount of CSF contained in the microspheres was 6840 units per 1 mg of gelatin microspheres, as determined by using $^{125}I$ labeled HK-CSF.

Gelatin microspheres without CSF were also prepared by the same procedure as described above, and the amount of glutaraldehyde per total amount proteins was 0.28 mg/mg protein.

EXAMPLE 2

The inhibitory activity of macrophages pretreated with the CSF-contained gelatin microspheres prepared according to Example 1 on the growth of target cells, P815 mostocytoma cells, was estimated as follows. $5 \times 10^5$ of mouse peritoneal macrophages, which are adherent cells in peritoneal exudate cells collected from mouse having injected intraperitoneally with thioglycollate 4 days prior to cell harvest, was suspended in 1ml of RPMI-1640 medium containing 10% fetal calf serum (FCS, and the aliquots of 1ml of cell suspension were seeded on 16 mm dishes of 24-well multidish culture plates. The CSF-contained gelatin microspheres, CSF-free gelatin microspheres, and native CSF were added to the macrophage monolayers incubated in 5%-$CO_2$/95% air at 37° C. for two days to activate macrophages. Then, the macrophage cultures were rinsed thoroughly with RPMI-1640 medium to remove native CSF and non-phagocytized CSF-containing gelatin microspheres before the addition of target cells. P815 mastocytoma cells, $2.5 \times 10^4$ in 1 ml of RPMI-FCS were added to the macrophage monolayers. The numbers of viable P815 mastocytoma cells was counted after culture for 38 br at 30° C. The growth inhibitory activity of macrophages towards P815 mastocytoma cells was evaluated according to the following formula.

$$\text{Precent growth inhibition} = \frac{\begin{array}{c}\text{Number of target cells} \\ \text{cultured with} \\ \text{untreated macrophage } \Delta\end{array} - \begin{array}{c}\text{Number of target cells} \\ \text{cultured with} \\ \text{activated macrophage } \Delta\end{array}}{\begin{array}{c}\text{Number of target cells cultured with} \\ \text{untreated macrophages}\end{array}} \times 100$$

The results are shown in Table 1.

TABLE 1

| Macrophage pretreatment in 1 ml medium containing | Percent growth inhibition |
| --- | --- |
| None | 0 |
| Gelatin microspheres containing CSF [440 U (64.3 μg)/ml] | 30.2 |
| CSF-free gelatin microspheres (64.3 μg/ml) | 0.6 |
| Native CSF (1000 U/ml) | 6.4 |
| Native CSF (440 U/ml) + CSF-free gelatin microspheres (64.3 μg/ml) | 1.0 |

As seen from the Table 1, the present CSF-contained gelatin microspheres activated the macrophages to exhibit a very high growth inhibitory activity on tumor cell growth, in contrast with native CSF, CSF-free gelatin microspheres, and a mixture thereof.

EXAMPLE 3

The assay method for macrophase activation as described in Example 2 was used to assess the dose-response relationship between the amount of CSF required to activate macrophages and the resulting antitumor activity. Gelatin microspheres containing different amounts of CSF were prepared according to Example 1. The C S F employed was prepared according to Reference Example 1. The dose responses for macrophage activation are shown in FIG. 3.

Figure 1:
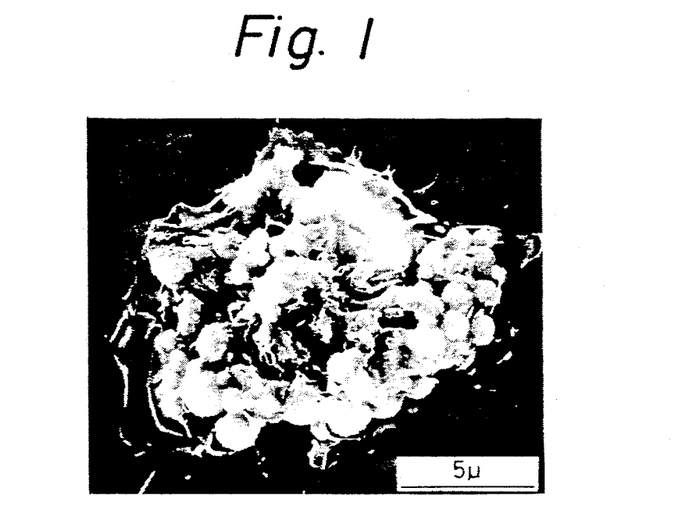
FIG. 1 is a scanning electron micrograph of a thioglycollate-induced mouse peritoneal macrophage 8 hours after incubation with gelatin microspheres containing mouse CSF.
Figure 2:
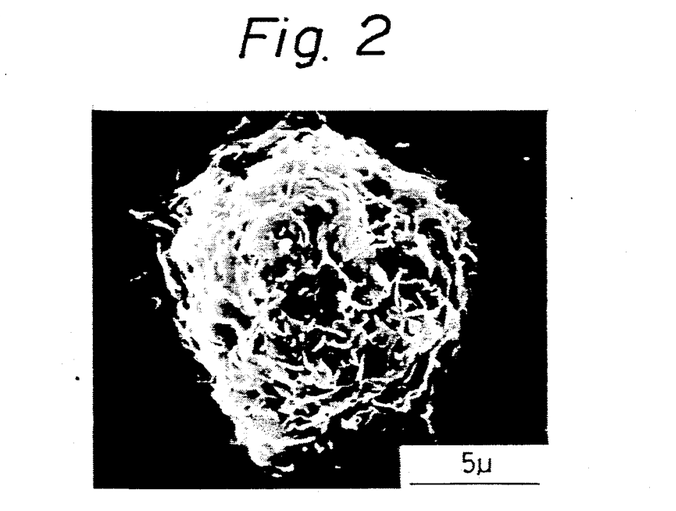
FIG. 2 is a scanning electron micrograph of a thioglycolate-induced mouse peritoneal macrophage before phagocytosis of gelatin microspheres containing mouse CSF.
Figure 3:
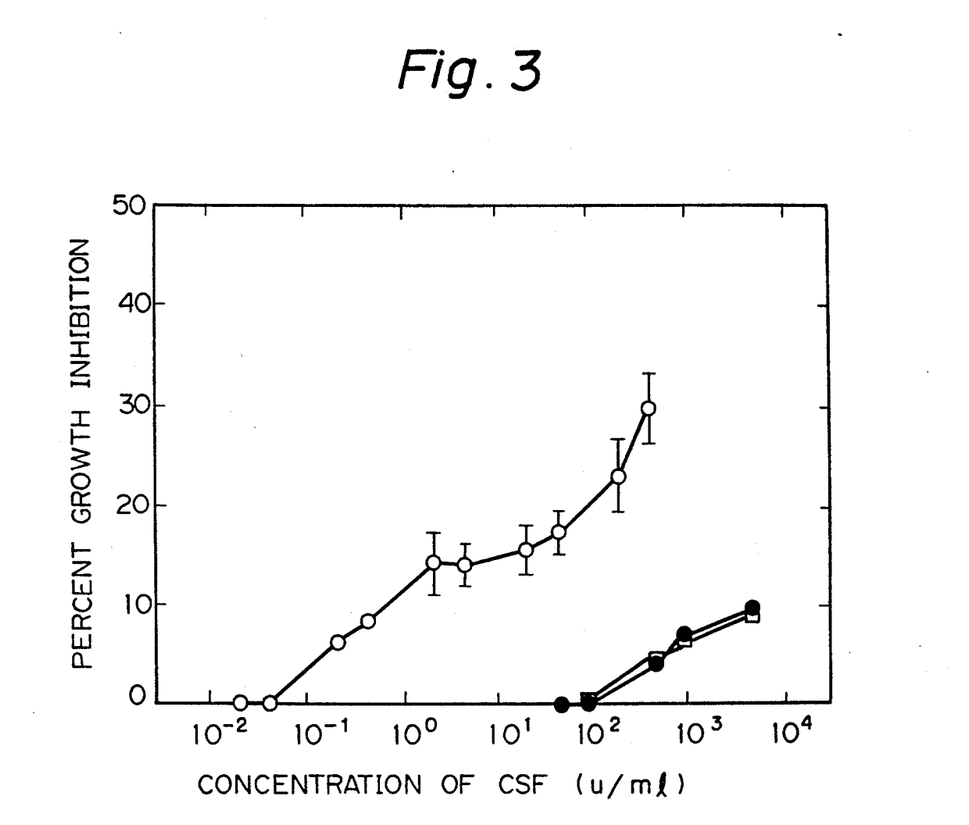
FIG. 3 shows the in vitro growth inhibitory activity of macrophages pretreated with crosslinked gelatin microspheres containing different doses of CSF. In this FIG., the symbol —•— represents a result for native CSF, —○— represents a result for crosslinked CSF-containing microspheres of the present invention, and —□— represents a result for a mixture of native CSF and gelatin microspheres without containing CSF.

As seen from FIG. 3, the total amount of CSF in the cultures required for macrophage activation by the present CSF-contained gelatin microspheres is approximately 10,000 times lower that by native CSF or by a mixture of native CSF and CSF-free gelatin microspheres. Besides, the addition of CSF-free microspheres had no effect on the activation induced by native CSF. The results clearly demonstrate that, the present CSF-contained microsphere enable macrophages to exhibit inhibitory activity on tumor cell growth far more efficiently than the native CSF.

EXAMPLE 4

The same procedure as described in Example 1 was used to prepare gelatin microspheres containing CSF except for the use of 1 ml of glutaraldehyde-saturated toluene solution (containing glutaraldehyde 0.05 mg/mg total proteins) was used. The amount of HK-CSF contained in 1 mg of the resulting gelatin microspheres was the equivalent to that described in Example 1.

EXAMPLE 5

Figure 4:
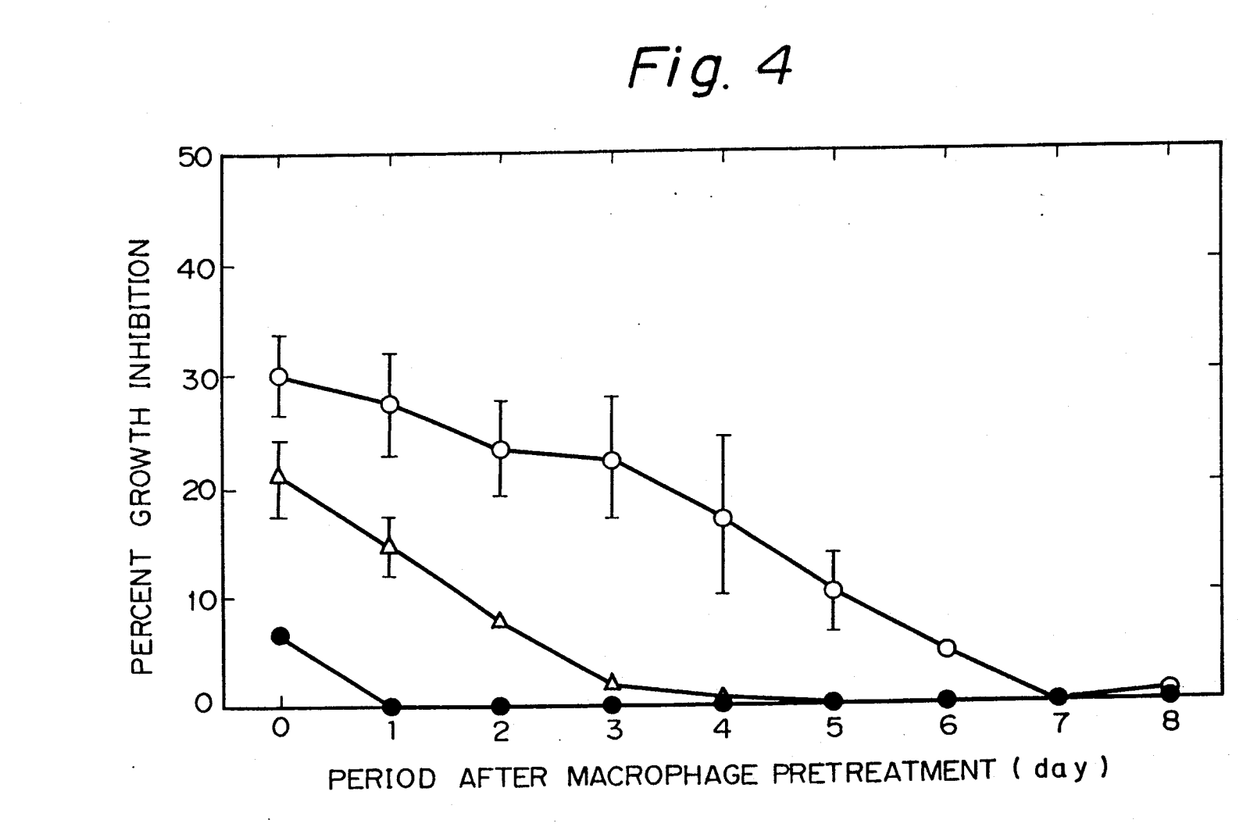
FIG. 4 shows descrement patterns of the active state of macrophages pretreated with native CSF and crosslinked gelatin microspheres containing CSF. In this FIG., the symbol —•— represents a result for 1000 units of native CSF, —○— represents a result for the present gelatin microspheres containing 440 units of CSF (G-I), and —△— represents a result for the present gelatin microspheres containing 440 units of CSF (G-II)

Macrophages were pretreated for 3 days with the gelatin microspheres containing 440 units of HK CSF, as prepared in Example 1 (G-I), and the gelatin microspheres containing 440 units of HK-CSF, as prepared in Example 4 (G-II), as well as 1,000 units of native HK-CSF, then thoroughly washed, and cultured in fresh medium. P815 mastocytoma cells were added to activated macrophages 1 to 8 days later to assess the durability of the activated state of macrophages. The results are shown in FIG. 4. As seen from FIG. 4, although the antitumor activity of macrophages pretreated with native CSF completely disappeared within 1 day, that of macrophages pretreated with the present CSF-contained gelatin microspheres maintained for more than two days. Moreover, the retention time of the activation can be regulated by changing the extent of cross-linking of gelatin microspheres with glutaraldehyde.

EXAMPLE 6

First, 0.28 g of sorbitan monooleate (Span 80) was dissolved in a mixture of 2.5 ml toluene and 2.5 ml chloroform, and to this organic solution, 0.2 ml of an aqueous solution containing 20 mg of gelatin and $1.38 \times 10^5$ units of M-CSF (abbreviated as Hu-CSF) isolated from human urine in Reference Example 2 was added and the mixture was homogenated by sonication at 10 W for 10 seconds. Then, the resulting emulsion was poured rapidly to 40 ml of a precooled solution of chloroform/toluene (25%/75%) containing 2 g of Span 80. Next, to the gelatin emulsion a 5 ml aliquot of the glutaraldehyde-saturated toluene, prepared according to Example 1 and the mixture was continuously stirred for 6 hours. Then the emulsion was centrifuged at 4,000 rpm for 5 minutes to collect the resulting gelatin microspheres containing CSF. The microspheres were successively washed with a chloroform/toluene (25%/75%) mixture, isopropanol, and PBS. The washing was repeated 4 times, and finally, the washed CSF-contained gelatin microspheres were suspended in PBS. The amount of CSF contained in the microspheres is 6840 units of Hu-CSF per 1 mg of gelatin microspheres.

EXAMPLE 7

The same experiment as described in Example 2 was conducted by use of the CSF-contained gelatin microspheres prepared in Example 6. The results are shown in Table 2.

TABLE 2

| Macrophage pretreatment in 1 ml medium containing | percent growth inhibition |
| --- | --- |
| None | 0 |
| Gelatin microspheres containing CFS [440 U (64.3 μg)/ml] | 23.2 |
| CSF-free Gelatin microspheres (64.3 μg/ml) | 4.9 |
| Native CSF (1000 U/ml) | 3.0 |
| Native CSF (440 U/ml) + CSF-free gelatin microspheres (64.3 μg/ml) | 0.6 |

As seen from Table 2, the present Hu-CSF-contained gelatin microspheres activated the microphages to exhibit a very high growth inhibitory activity on tumor cell growth in contrast with native Hu-CSF, CSF-free gelatin microspheres, and a mixture thereof.

EXAMPLE 8

The assay procedure as described in Example 2 was conducted to assess the dose response relationship between the amount of Hu-CSF required to activate macrophages and the resulting antitumor activity. Gelatin microspheres containing different amounts of H-CSF prepared according to Reference Example 2, were prepared according to Example 6. The dose responded for macrpophage activation are shown in FIG. 5.

Figure 5:
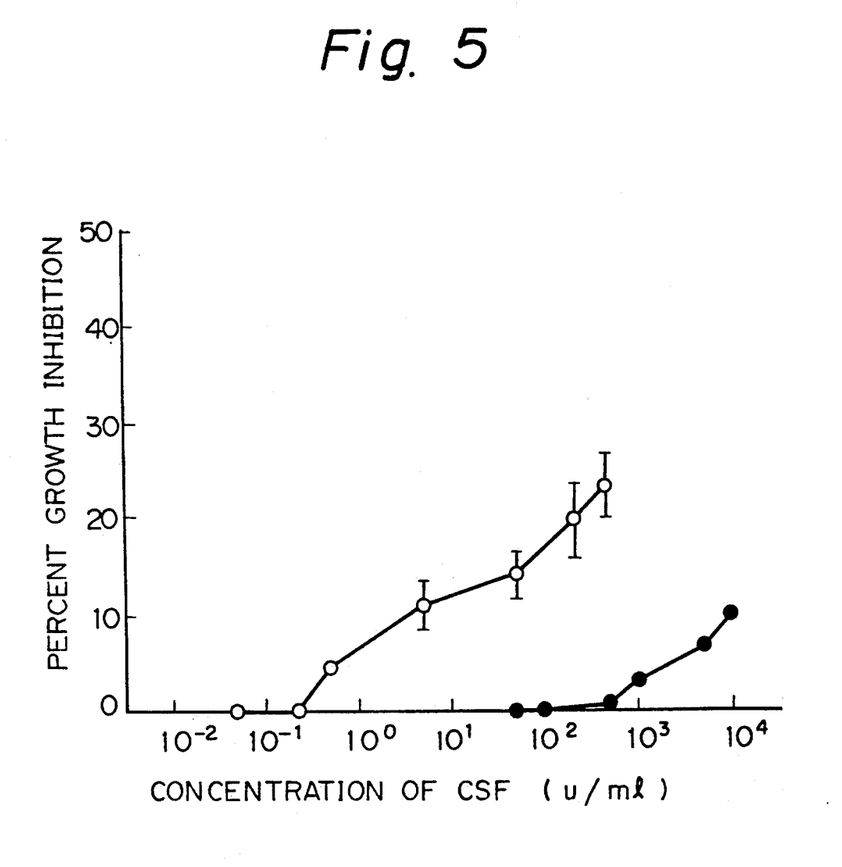
FIG. 5 shows the in vitro growth inhibitory activity of macrophages pretreated with crosslinked gelatin microspheres containing different doses of CSF of human urine origin: The symbol —•— represents a result for native CSF, and —○— represents a result for crosslinked CSF-containing gelatin microspheres of the present invention.

As seen from FIG. 5, the present CSF-contained gelatin microspheres could activates macrophages to inhibit tumor cell growth, to a similar extent to the macrophage activation induced by native CSF, at a concentration of CSF about 5,000 times lower than that for native CSF. The results clearly demonstrate that the present microspheres enable macrophages to activate to inhibit tumor cell growth in contrast to native CSF.

EXAMPLE 9

First, 10 mg of gelatin (alkaline form, pI 4.9, Nitta Gelatine, Japan) was dissolved in 10 ml of phosphate-buffered saline solution (PBS, pH 4.7), and to the solution HK-CSF prepared according to Reference Example 1, or Hu-CSF prepared according to Reference Example 2, was added in an amount of $6.9 \times 10^5$ units, and the mixture was stirred at 4° C for 10 minutes. Next, 10 mg of a water soluble carbodiimide, i.e., 1-ethyl-3-(3-dimethylaminopropyl) carbodiimide hydrochloride (Nakarai Tesque) was added to the mixture, and a reaction was further carried out at 4° C. for 19 hours. Then the reaction mixture was dialyzed, and sterilized by filtration through a 0.22 μm Millex-GS milipore filter to obtain a water-soluble CSF-gelatin conjugate. When the same procedure was carried out by using $^{125}$I-CSF, the recovery of gelation microspheres containing CSF was 42.5% and the amount of CSF contained in the water-soluble CSF-gelatin conjugates was 68940 units of CSF per 1 mg of gelatin microspheres, for both of HK-CSF and Hu-CSF.

EXAMPLE 10

The inhibitory activity of macrophage pretreated with the water soluble CSF (HK-CSF) gelatin conjugates prepared in Example 9 on the growth of target cells, P815 mastocytoma cells, was evaluated as follows. The water soluble CSF (HK-CSF) gelatin conjugate, gelatin and/or native CSF (HK-CSF) were added to the macrophage monolayers prepared according to Example 2, and incubated in 5%-$CO_2$/95% air at 37° C. for two or three days to activate macrophages. Next, the macrophage cultures were rinsed thoroughly with RPMI-1640 medium to completely remove the added macrophage activator. $2.5 \times 10^4$ P815 mastocytoma cells in 1 ml of RPMI-FCS were added to the macrophage monolayers. The number of viable P815 mastocytoma cells was counted after culture for 48 hr at 37° C. The growth inhibitory activity was evaluated as described in Example 2. The results are shown in Table 3.

TABLE 3

| Macrophage pretreatment in 1 ml medium containing | 2 days Pre-treatment | | 3 days Pretreatment | |
|---|---|---|---|---|
| | LPS (−) | LPS (+)[a] | LPS (−) | LPS (+) |
| None | 0 | 1.0 | 0 | 0.8 |
| Native HK-CSF (1000 u/ml) | 7.5 | 16.2 | 6.9 | 18.9 |
| HK-CSF (586 u)-gelatin conjugate (8.5 μg/ml) | 26.2 | 30.3 | 24.8 | 32.6 |
| CSF-free Gelatin (8.5 μg/ml) | 0.2 | 0.6 | 0.1 | 0.8 |
| CSF-free Gelatin (8.5 μg/ml) + native HK-CSF (586 u/ml) | 0.8 | 0.4 | 0.6 | 1.0 |

[a] 10 ng/ml of polyliposaccharide (LPS) is present in the pretreatment.

As seen from Table 3, the present water-soluble CSF-gelatin conjugate activated macrophages to exhibit a very high growth inhibitory activity on tumor cell growth, in contrast with native CSF and CSF-free gelatin. In addition, only mixing of CSF with gelatin did not induce macrophage activation activity.

EXAMPLE 11

The same procedure as described in Example 10 was conducted to assess the ability of the water soluble CSF (HK-CSF)-gelatin conjugate to activate macrophage as Rl fibrosarcoma cells was used as target cells instead of P815 mastocytoma cells. The antitumor activity of macrophages after two days pretreatment are shown in Table 4.

TABLE 4

| Macrophage pretreatment in 1 ml medium containing | Percent growth inhibition | |
|---|---|---|
| | LPS (−) | LPS (+)[a] |
| None | 0.6 | 0.7 |
| Native HK-CSF (1000 u/ml) | 12.6 | 27.3 |
| HK-CSF (586 u)-gelatin conjugate (8.5 μg/ml) | 26.4 | 34.1 |
| CSF-free Gelatin (8.5 μg/ml) | 0.8 | 1.2 |
| CSF-free Gelatin (8.5 μg/ml) + native HK-CSF (586 u/ml) | 0.7 | 1.6 |

10 ng/ml of LPS is present in the pretreatment.

EXAMPLE 12

The inhibitory activity of macrophage pretreated with the CSF (Hu-CSF)-gelatin conjugate prepared in Example 9 on the growth of P815 mastocytoma or Rl fibrosarcoma cells was evaluated as-follows: Macrophages prepared according to the procedure in Example 2 was incubated with the water soluble CSF (Hu-CSF)-gelatin conjugate, native CSF (Hu-CSF), and/or CSF-free gelatin in 5%-CO$_2$/95% air at 37° C. for two days to activate. Next, the macrophages cultures were rinsed thoroughly with RPMI-1640 medium to completely remove the added macrophage activator. 2.5×10$^4$ P815 mastocytoma cells in 1 ml of RPMI-FCS were added to the macrophage monolayers. The inhibitory activity of macrophages on the growth of P815 mastocytoma or Rl fibrosarcoma cells was evaluated as described in Example 2.
The results are shown in Table 5.

TABLE 5

| Macrophage pretreatment in 1 ml medium containing | Percent growth inhibition | | | |
|---|---|---|---|---|
| | P815 mastocytoma | | Rl fibrosarcoma | |
| | LPS (−) | LPS (+)[a] | LPS (−) | LPS (+) |
| None | 0 | 1.0 | 0.6 | 0.7 |
| Native Hu-CSF | 0.2 | 2.7 | 5.4 | 6.0 |
| Hu-CSF (586 u)-gelatin conjugate (8.5 μg/ml) | 28.6 | 32.2 | 20.0 | 27.5 |
| CSF-free Gelatin (8.5 μg/ml) | 0.2 | 0.6 | 0.8 | 1.2 |
| CSF-free Gelatin (8.5 μg/ml) + native Hu-CSF (586 u/ml) | 0.2 | 1.6 | 3.2 | 2.4 |

[a] 10 ng/ml of LPS is present in the pretreatment.

EXAMPLE 13

The assay procedure for macrophage activation as described in Example 2 was used to assess the dose-response relationship between the amount of CSF required to activate macrophages and the resulting anti tumor activity. A water-soluble CSF (HK-CSF)-gelatin conjugate containing different amounts of HK-CSF which was prepared according to Reference Example 1, was prepared according to Example 9. The results are shown in FIG. 6.

Figure 6:
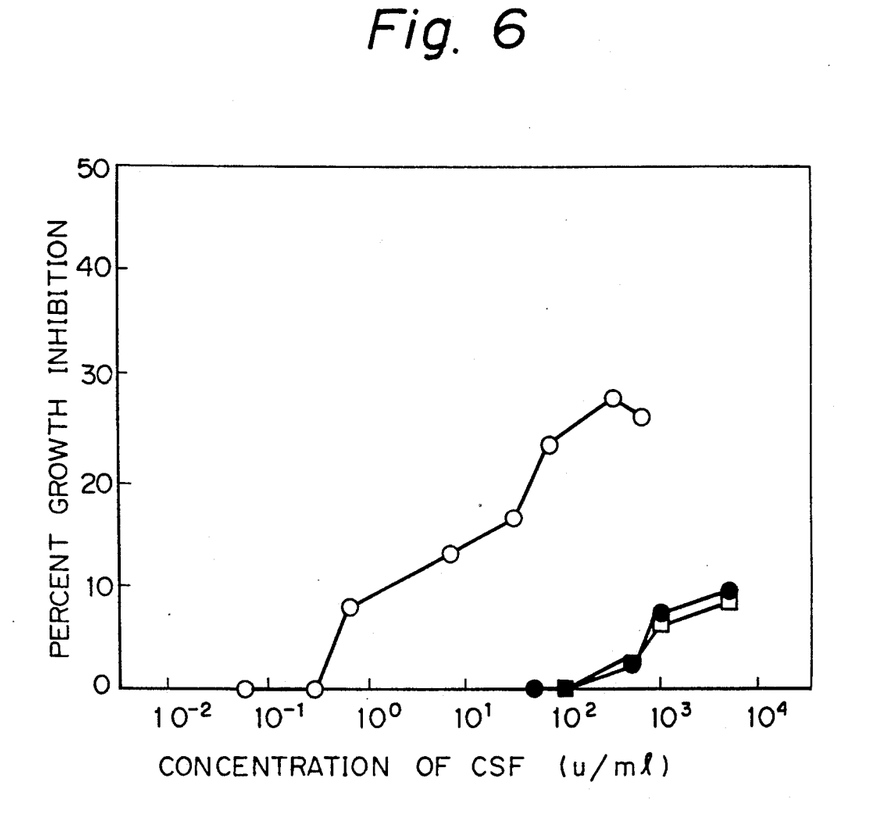
FIG. 6 shows the in vitro growth inhibitory activity of macrophages pretreated with CSF-gelatin conjugates containing different doses of CSF. In this FIG., the symbol —•— represents a result for native CSF, —○— represents a result for CSF-gelatin conjugate, and —□— represents a result for a mixture of native CSF and CSF-free gelatin.

As seen from FIG. 6, the total amount of CSF in the cultures required for macrophage activation by the present CSF-gelatin conjugate is approximately 2,000 times lower than that by native CSF or by a mixture of native CSF and CSF-free gelatin. The results clearly demonstrate that the present water soluble CSF (HK-CSF)-gelatin conjugate is more effective in activating macrophages than the native CSF (HK-CSF) control, and a mixture of native CSF (HK-CSF) and gelatin.

EXAMPLE 14

Figure 7:
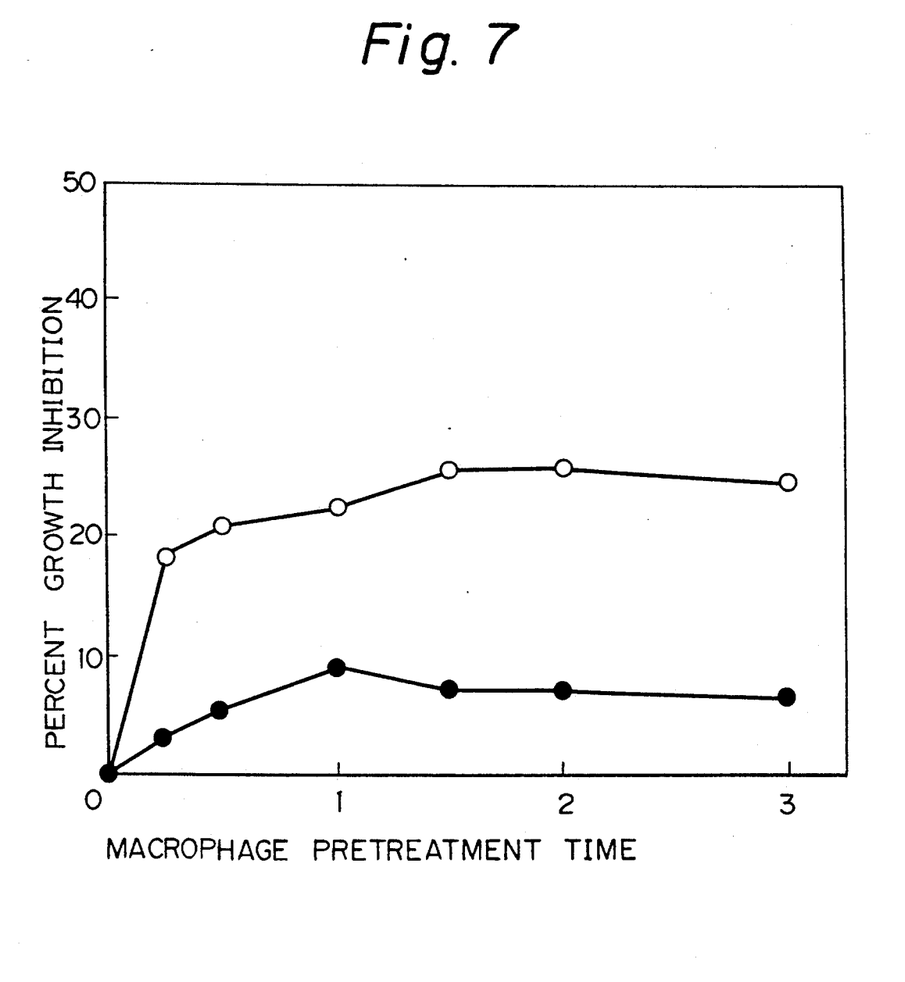
FIG. 7 shows time course of the in vitro growth inhibiting activity of macrophages pretreated with CSF-gelatin conjugates. In this FIG., the symbol —•— represents a result for 1000 units of native CSF, and —○— represents a result for a CSF-gelatin conjugate containing 586 units of CSF.

To study the time course of macrophage activation, macrophages were pretreated for different time periods to 3 days with a water soluble CSF (HK-CSF)-gelatin conjugate prepared in Example 9 or native CSF (HK-CSF). The cell inhibitory activity of the macrophages on the growth of P815 mastocytoma cells is shown in FIG. 7. High efficiency of the present water soluble CSF (HK-CSF)-gelatin conjugate for macrophage activation was revealed in the short pretreatment time of macrophages, in comparison with native CSF.

REFERENCE EXAMPLE 1

PREPARATION OF HK-CSF

First, 3×10$^8$/roller bottle of HK-CSF cells derived from mouse fibroblast were cultured in DM-160 medium containing 1 mM lithium chloride and 0.1% sodium bicarbonate at 37° C. for 3 days to obtain a culture supernatant. The supernatant contained 3500 units of CSF activity. The CSF activity was assayed by an in vitro mouse bone narrow culture method (Shikita, M. et al., Journal of Cellular Physiollogy, 109, 161–169, 1981). One unit of CSF is defined as the activity producing one colony. The supernatant was adjusted to a pH of 4.5 by 10% phosphoric acid, and the resulting precipitate was eliminated. The supernatant was purified by EDTA-cellulose chromatography, phenyl sepharose chromatography, Sephacryl S-300 and Superose 12 column chromatography to obtain M-CSF. The M-CSF thus obtained had a molecular weight of 100,000+1,000 as determined by SDS-PAGE analysis, a specific activity of 1.8×10$^8$ U/mg protein wherein a quantity of protein was determined using BCA Protein Assay Reagent (Pierce Chemical Company) (Smith, P.K. et al., Analytical Biochemstry 150, 76-85, 1985), and an ability to form only macrophage colonies in the in-vitro mouse bone marrow culture method.

REFERENCE EXAMPLE 2

PREPARATION OF HU-CSF

First, 10,000 l of urine from mature male human was treated with 20 kg of granular hydrous silicic acid (a brand name "White Carbon" (Tokuyama Soda, Tokyo)) to adsorb proteins in the urine on the silicic acid. The proteins were extracted with 1% aqueous ammonia, and precipitated by an 80% saturation of ammonium sulfate. The precipitate was dissolved in water, the solution was adjusted to a pH of 4.5 and heated at 60° C for 10 hours. The precipitate formed was eliminated by centrifugation, and the supernatant was desalted to obtain a crude CSF solution. The solution was purified by DEAE-cellulose chromatography, phenyl Sepharose chromatography, Sephacryl S-300 chromatography, Superose 12 chromatography, and μ-Bondapak C18 column (Waters) chromatography to obtain M-CSF, having a molecular weight of 82,000±6,000 as determined by SDS-PAGE analysis, a specific activity of $1.3 \times 10^8$ U/mg protein, and an ability to form only macrophage colonies in the in vitro mouse bone marrow culture method.

We claim:

1. A conjugate comprising CSF and gelatin, wherein the conjugate is a water-soluble CSF-gelatin conjugate.

2. A conjugate according to claim 1, wherein the CSF is macrophage CSF.

3. A process for the production of water soluble CSF-gelatin conjugate comprising the step of:
    coupling CSF to gelatin in an aqueous medium with a water-soluble carbodiimide to form a water-soluble conjugate.

4. A pharmaceutical preparation available for an inhibition of tumor cell growth, comprising a CSF-gelatin conjugate according to claim 1.

* * * * *